(12) United States Patent
Prushinskaya et al.

(10) Patent No.: US 8,433,400 B2
(45) Date of Patent: Apr. 30, 2013

(54) METHOD AND PORTABLE DEVICE FOR TREATING SKIN DISORDERS

(76) Inventors: Marina Prushinskaya, Farmington, MI (US); Leonid Kaplan, Farmington, MI (US)

(*) Notice: Subject to any disclaimer, the term of this patent is extended or adjusted under 35 U.S.C. 154(b) by 450 days.

(21) Appl. No.: 12/739,659

(22) PCT Filed: Oct. 23, 2008

(86) PCT No.: PCT/US2008/080977
§ 371 (c)(1),
(2), (4) Date: Apr. 23, 2010

(87) PCT Pub. No.: WO2009/055581
PCT Pub. Date: Apr. 30, 2009

(65) Prior Publication Data
US 2010/0241059 A1    Sep. 23, 2010

Related U.S. Application Data

(60) Provisional application No. 61/000,135, filed on Oct. 24, 2007.

(51) Int. Cl.
*A61N 1/30* (2006.01)
(52) U.S. Cl.
USPC ............... 604/20; 604/19; 607/145; 607/150

(58) Field of Classification Search ............ 604/19, 604/20; 607/145, 150; 600/573
See application file for complete search history.

(56) References Cited

U.S. PATENT DOCUMENTS

| 4,731,049 | A | * | 3/1988 | Parsi ............................. 604/20 |
| 5,156,591 | A | * | 10/1992 | Gross et al. .................. 604/20 |
| 5,538,503 | A | | 7/1996 | Henley |
| 5,658,247 | A | | 8/1997 | Henley |
| 6,157,858 | A | | 12/2000 | Gross et al. |
| 7,137,975 | B2 | | 11/2006 | Miller et al. |

OTHER PUBLICATIONS

International Search Report dated Apr. 30, 2009, of corresponding PCT Appn. No. PCT/US2008/080977, 2 pgs.

* cited by examiner

*Primary Examiner* — Laura Bouchelle
(74) *Attorney, Agent, or Firm* — Brooks Kushman P.C.

(57) ABSTRACT

A device for treating a skin condition is provided. The device comprises a delivery system for administering a composition to the skin disorder. The delivery system includes an electrode for delivering a composition to the skin of a person and a counter electrode. The device also includes a drainage system which includes a channel for removing material from a person's skin and a pump in communication with the channel. The device further includes a control system for powering and controlling the electrode system.

10 Claims, 5 Drawing Sheets

METHOD AND PORTABLE DEVICE FOR TREATING SKIN DISORDERS

CROSS-REFERENCE TO RELATED APPLICATION

This application claims the benefit of U.S. provisional application Ser. No. 61/000,135 filed Oct. 24, 2007.

BACKGROUND OF THE INVENTION

1. Field of the Invention

The present invention relates to an apparatus and method for treating skin disorders such as acne, furuncles, and the like.

2. Background Art

Acne is a term for a medical condition of plugged pores typically occurring on the face, neck, and upper torso. The plugged pores result in blackheads, whiteheads, pimples or deeper lumps such as cysts or nodules. Severe cases of acne can result in permanent scarring or disfiguring. Acne is often associated with both males and females during adolescence or puberty. Typically, acne begins between the ages of ten and thirteen and usually lasts for five to ten years. For the majority of the population, acne dissipates naturally by the early twenties. However, for a minority, acne is severe enough to require some treatment by a physician.

Acne occurs when the oil glands of the skin called sebaceous glands produce an increased amount of oil. The sebaceous glands are connected to canals in the skin called hair follicles that terminate in openings in the skin called pores. An increased amount of oil secreted by the sebaceous glands is caused by an increase in androgen hormones in both males and females during adolescence or puberty. Accompanying this increase is an increase in the shedding of the skin lining the hair follicles. The increase in the amount of secreted oil in combination with the increase in the shedding of the skin lining the hair follicles increases the likelihood of the pores being clogged by the shedding skin. A pore clogged by the shedding skin is referred to as a comedo.

Bacteria naturally occurring on the skin are known as *propionibacterium acnes* (*P. acnes*). The *propionibacterium acnes* invade the clogged follicles and grow in the mixture of oil and cells in the hair follicle. The *propionibacterium acnes* produce chemicals that stimulate inflammation resulting in acne. Acne lesions range in severity from blackheads, whiteheads and pimples to more serious lesions such as deeper lumps, cysts and nodules. In many instances, the inflammation within the acne lesion provides an opportunity for secondary infections to invade and grow in the inflamed hair follicle. Some of these secondary infections can be more serious and more resistant to treatment than the primary *propionibacterium acnes* infection.

Many treatments and medications have been proposed by the prior art to control, reduce or eliminate acne. Examples of conventional topical medications include acne lotion containing benzoyl peroxide, salicylic acid or sulfur. Examples of conventional oral medications include tetracycline, doxycycline, minocycline or erythromycin. In severe cases, isotretinoin is often prescribed orally when the severe acne has not responded to other medication. It is believed these antibiotics reduce the *propionibacterium acnes* in the hair follicle to reduce the underlying cause of the acne. Among the more unconventional treatments and medications proposed by the prior art to control, reduce or eliminate acne include a light chemical peel. In a light chemical peel, glycolic acid and other chemical agents are applied to the skin to loosen blackheads and decrease acne papules. Other unconventional treatments include the use of ultraviolet light therapy.

Other suggested acne treatments include the use of a citrus component in medications for affecting various beneficial results. Citrus components have been used as an ingredient for various products such as cosmetic product and/or other medicinal productions.

Accordingly, there is still a need for improved methods for treating acne and acne related skin conditions.

SUMMARY

The present invention solve one or more problems of the prior art by providing in at least one a device for treating acne, furuncles and similar skin disorders which are characterized by blocked channels in the skin. The device of this embodiment comprises a delivery system for administering a composition to the skin disorder. The delivery system includes an electrode for delivering a composition to the skin of a person and a counter electrode. The device also includes a drainage system which includes a channel for removing material from a person's skin and a pump in communication with the channel. The device further includes a control system for powering and controlling the electrode system.

In another embodiment, a device for treating a skin disorder is provided. The device of this embodiment includes a first delivery system for administering a first composition to the skin disorder and a second delivery system for administering a second composition to the skin disorder. The first delivery system comprises a first electrode for delivering the first composition and an optional first counter electrode. The second delivery system comprises a second electrode for delivering the second composition and an optional second counter electrode. The device also includes a control system for powering and controlling the first and second delivery systems.

In another embodiment, a device for treating a skin disorder is provided. The device of this embodiment includes a first delivery system for administering a first composition to the skin disorder and a second delivery system for administering a second composition to the skin disorder. The first delivery system comprises a first electrode for delivering the first composition and an optional first counter electrode. The second delivery system comprises a second electrode for delivering the second composition and an optional second counter electrode. The device also includes a drainage system. The drainage system has a channel for removing material from a person's skin; and a pump in communication with the channel; The device also includes a control system for powering and controlling the first and second delivery systems.

DETAILED DESCRIPTION OF THE PREFERRED EMBODIMENT(S)

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

Figure 1A:
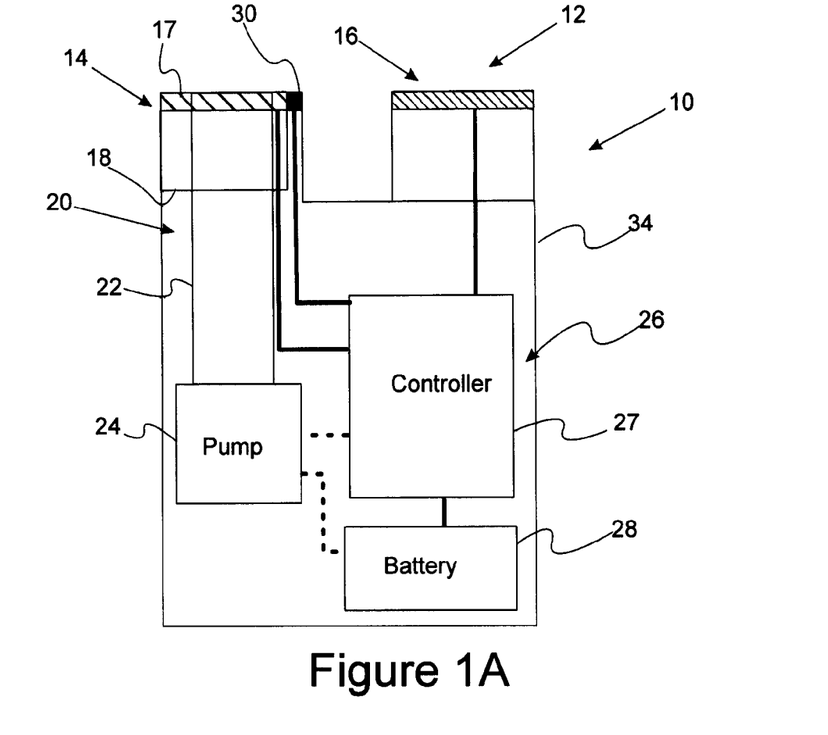
FIG. 1A is a schematic providing the components of a portable device for treating acne and other skin conditions.
Figure 1B:
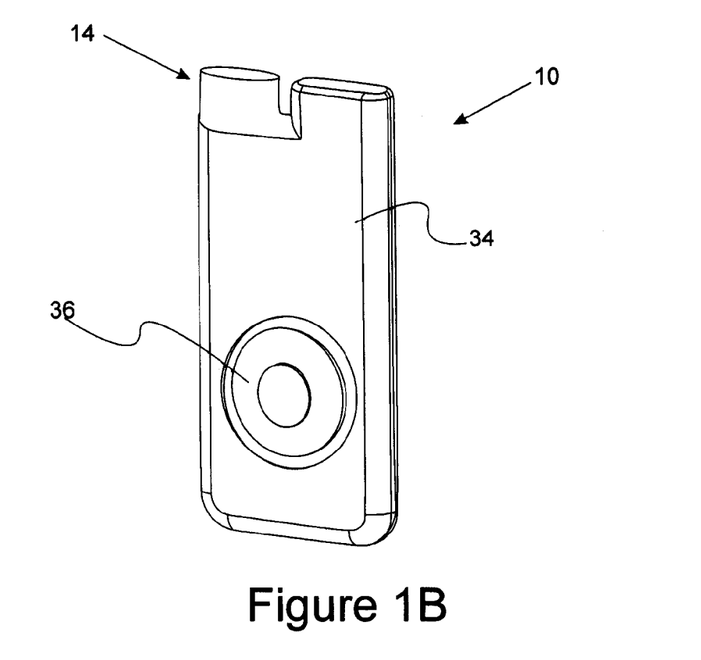
FIG. 1B is a perspective view of the device of FIG. 1A.

With reference to FIGS. 1A and 1B, illustrations of a portable device for treating skin conditions such as acne are provided. FIG. 1A is a schematic providing the components of the device. FIG. 1B is a perspective view of the device. Portable device 10 includes electrode system 12. Electrode system 12 includes electrode 14 and counter or dispersive electrode 16. Electrode 14 include permeable layer 17 and receptacle 18 which holds a composition to be delivered to a person's skin through permeable layer 17. Electrode 14 is used for delivery of the composition to the skin of a person. In a variation, device 10 further includes drainage system 20 for removing material from the skin condition that is treated. Drainage system 20 includes channel 22 for removing material from a person's skin and pump 24 in communication with channel 22. Device 10 also includes control system 26 for powering and/or controlling the electrode system 12. In a refinement, the drainage system 20 is also controlled and powered by control system 26. In another refinement, the drainage system is manually operated (e.g., syringe-like pump). In a variation of the present embodiment, control system 26 also includes controller 27 and voltage source 28 which is typically a battery. Device 10 also includes casing 34 and a user operated control interface 36. FIG. 1B depicts a user operated interface which is a button. In another refinement, control interface 36 include one or more push button controllers.

Still referring to FIG. 1A, in a variation of the present embodiment, portable device 10 further includes sensor 30 which is in communication with control system 26.

Figure 2A:
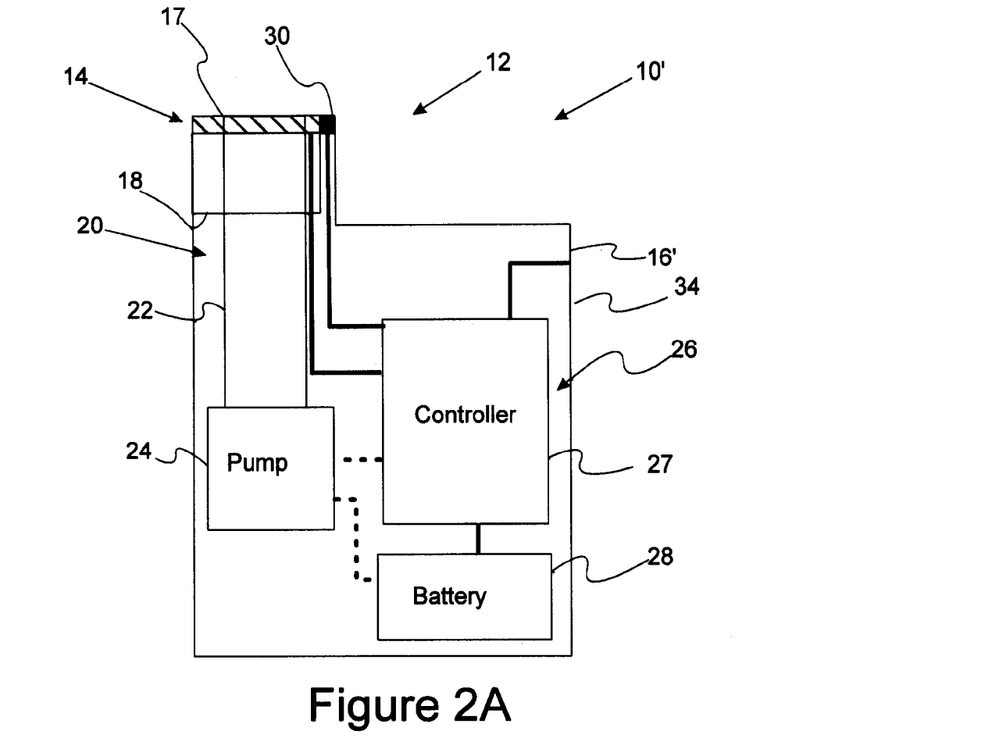
FIG. 2A is a schematic providing the components of a portable device for treating acne and other skin conditions.
Figure 2B:
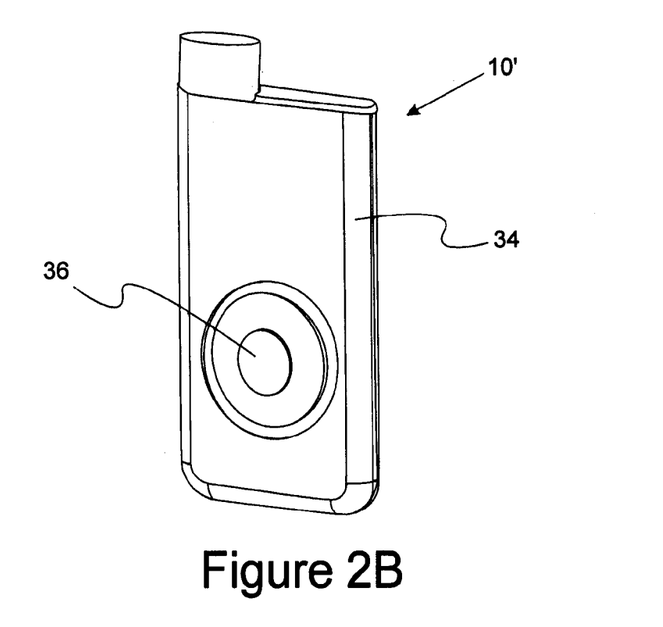
FIG. 2B is a perspective view of the device of FIG. 1A.

With reference to FIGS. 2A and 2B, illustrations of a variation portable device for treating skin conditions such as acne are provided. FIG. 2A is a schematic providing the components of the device. FIG. 2B is a perspective view of the device. In this variation, portable device 10' integrates the counter electrode 16' in the casing 34 of device 10.

Portable device 10 can be configured in a variety of different forms. For example, device 10 can be a hand-held device, finger-mounted device, head-mounted device, pocket device, distributed device, or any combination thereof.

As set forth above, device 10 includes voltage source 28. Example of voltage source 28, include DC voltage sources, bipolar DC voltage sources, unipolar sources of rectified AC voltage, bipolar sources of rectified AC voltage, sources of non-rectified AC voltage, or any combinations thereof. Moreover, the voltage or current applied to the skin at least one of the following characteristics: unchangeable unipolar voltage or current, variable magnitude unipolar voltage or current, unipolar repeatable pulses, repeatable sequences of unipolar pulses, unipolar varying pulses, alternating bipolar voltage or current of same magnitude, alternating bipolar voltage or current with asymmetrical magnitudes, bipolar repeatable pulses, repeatable sequences of bipolar pulses, and bipolar varying pulses. In a further refinement, the applied waveform is substantially an impulse in form; a practical approximation of a "Kronecker delta function" when viewed in the context of discrete time events; a practical approximation of a "Dirac delta function" when viewed in the context of continuous time events; substantially rectangular or trapezoid with essentially a nearly flat top; substantially a positive or negative going single pulse; a combination of positive and negative pulses; a pulse of sinusoidal waves; decaying pulses of all types listed above; or any combinations thereof. The polarity of the voltage and current applied the skin depends on needs of current step of treatment. The polarity may be substantially a positive or negative going single pulse; a combination of positive and negative pulses; a pulse of sinusoidal waves; or any combinations of those.

As set forth above, device 10 also includes control system 26. In a variation, control system 26 performs one or more of the following operations: determination of level of inflammation of acne; establishing the parameters for treatment; determination of content of the active solution suitable for the treatment; controlling and modifying the parameters for treatment in the process of the treatment; terminating the treatment as soon as the blockage of the channel is disrupted; controlling the process of drainage of degraded matter from the channel, process of disinfecting and process of healing of the channel; and providing control for masking an area of affected skin for a period of healing.

In another variation, parameters for treatment that are subject to control include accumulated duration of treatment, duration of current treatment session, magnitude of applied voltage or current, character of voltage or current, duration and frequency of pulses of voltage or current, waveform of pulses of voltage or current, slew rates of transition periods, polarity of voltage or current, and dose of electrical charge delivered to the treated area. Slew rate in transition periods may be from 0.001 V per second to 1,000 V per second, or from 0.001 mA per second to 1,000 mA per second. Polarity of voltage and current depends on needs of current step of treatment, and may be: substantially a positive or negative going single pulse; a combination of positive and negative pulses; a pulse of sinusoidal waves; or any combinations of those. Dose of electrical charge delivered to the treated skin disorder during the treatment session may be from 1 mA•min to 80 mA•min.

Portable device 10 may also include one or more additional component devices for enhancing effectiveness. Examples of such component devices, but are not limited to, devices for diagnosing, devices for operating, devices for drainage, devices for disinfecting, devices for healing, and devices for masking.

Figure 3A:
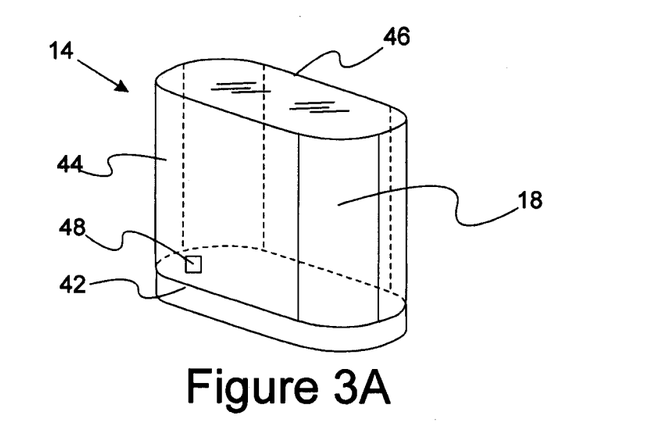
FIG. 3A is a schematic perspective view of a variation in which an electrode includes a receptacle that holds the composition to be applied to the skin.
Figure 3B:
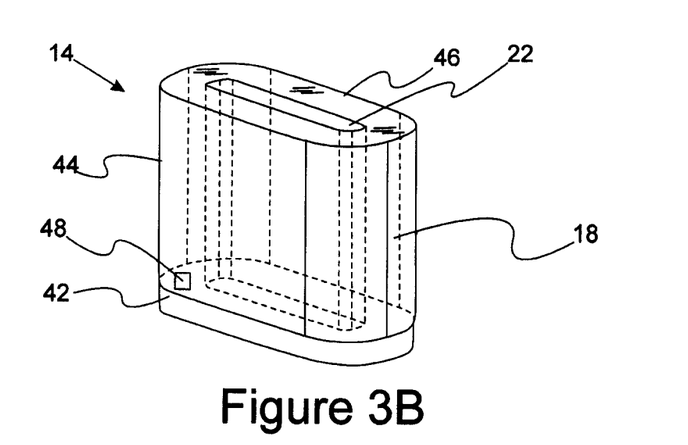
FIG. 3B is a schematic perspective view of a variation of an electrode having a channel for removing material from the skin is provided.
Figure 3C:
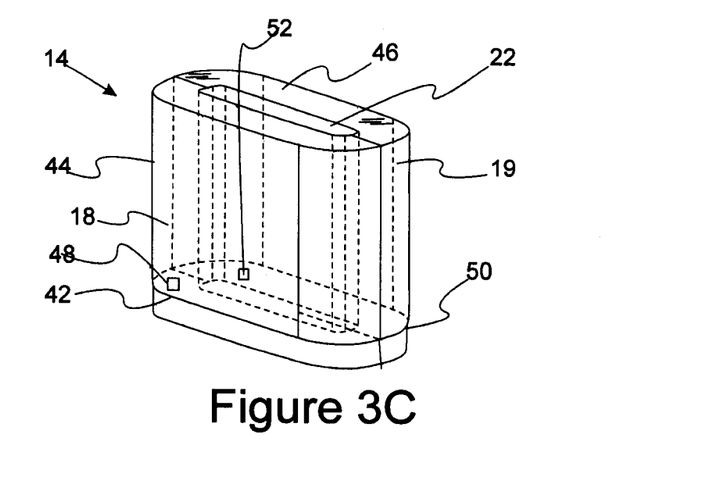
FIG. 3C is a schematic perspective view of a variation of an electrode having two receptacle and a channel for removing material from the skin is provided.

Device 10 includes electrode 14 which delivers a composition to the skin. In a variation, electrode 14 is an electrophoretic electrode and in particular an iontophoretic electrode. U.S. Pat. Appl. No. 20080154179 provides examples of iontophoretic systems and electrodes that can be used in the present application. The entire disclosure of this application is hereby incorporated by reference. FIG. 3A-3C provide several variations of electrode 14. FIG. 3A provides a schematic perspective view of a variation in which electrode 14 includes receptacle 18 which holds the composition to be applied to the skin. In a refinement, base wall 42 is made from a semi-permeable membrane or any other barrier capable of holding the active solution while allowing the passage of ions, radicals or molecules to contact the skin. Examples of suitable materials include porous resins such as polyester. In a refinement, at least a portion of walls 44 or 46 are covered with electroconductive material so that the material is in direct contact with base wall 42. In another refinement, terminal 48 connects base wall 42 with the voltage source.

With reference to FIG. 3B, a schematic perspective view of a variation of electrode 14 having a channel for removing material from the skin is provided. Electrode 14 includes receptacle 18 which holds the composition to be applied to the skin. Channel 22 passes through receptacle 18 allowing material to be withdrawn. Base wall 42 is made from a semipermeable membrane or any other barrier capable of holding the active solution while allowing the passage of ions, radicals or molecules to contact the skin. In a refinement, at least a portion of walls 44 or 46 are covered with electroconductive material so that the material is in direct contact with base wall 42. In another refinement, terminal 48 connects base wall 42 with the voltage source.

With reference to FIG. 3C, a schematic perspective view of a variation of electrode 14 having two receptacle and a channel for removing material from the skin is provided. Electrode 14 includes receptacles 18, 19 each of which holds a composition to be applied to the skin. Channel 22 passes through the combinations of receptacles 18, 19 allowing material to be withdrawn. Base wall 42 caps the end of receptacle 18 and is made from a semi-permeable membrane or any other barrier capable of holding the active solution while allowing the passage of ions, radicals or molecules to contact the skin. Base wall 50 caps the end of receptacle 19 and is made from a semi-permeable membrane or any other barrier capable of holding the active solution while allowing the passage of ions, radicals or molecules to contact the skin. At least a portion the interior walls of receptacles 18 and 19 are covered with electroconductive material so that the material is in direct contact with base wall 42. In another refinement, terminals 48, 52 connects base wall 42, 50 with the voltage source, respectfully. In this variation material from receptacles 18 and 19 can be independently operated allow the compositions therein, which may be different, to be delivered at different times.

In another refinement of the variations of FIGS. 3A, 3B, and 3C, the a substantial portion of the respective receptacles are filled with or defined by the semi-permeable material (i.e, resins such as polyester).

Receptacles 18, 19 are made as: permanent receptacle filled with active solution as needed; disposable receptacle preliminary filled with active solution; disposable receptacle preliminary filled with liquid component of active solution; disposable receptacle preliminary filled with solid component of active solution; blank disposable receptacle; or any combination of those. In a refinement, the active solution in amount between 0.1 and 3 cc. Components of the active ingredients contained in the receptacle can be added in the following forms: liquid introduced from additional vessel; solid element; tablet, capsule or pellet; molten solid element; disrupted gel capsule or microspheres filled with the component; disrupted impermeable barrier between components; unwrapped roll of tape holding the component; or any combination of those.

In another variation, the receptacles set forth above contain an active solution to be applied to a person's skin selected from the group consisting of solutions for disruption of blockage of the acne channel, solutions facilitating the drainage of degraded matter from the channel, solutions for disinfecting the channel, solutions for healing the channel, solutions for masking the area of affected skin, and multi-functional solutions. In other embodiments, the receptacle includes sections for multiple different active solutions. These receptacles may also comprise the section for drainage of degraded matter. The receptacles may have one electrode; individual electrodes in independent sections having different active solutions; a channel supplying active solutions to separate electrophoretic electrode; or any combination thereof.

The active solution may be produced within the receptacle prior to or during the treatment in the following ways: adding at least one component of the active solution into the receptacle; dissolving at least one component of the active solution; chemical reaction between components of the active solution; decomposition of at least one component of the active solution; or any combination thereof.

The following components can be added to produce the active solution within the receptacle: solvent, liquid component, gel component, solid component, or any combination of those. The following components can be dissolved to produce the active solution within the receptacle: liquid component, gel component, solid component, or any combination of those. The following components may be reacting to produce the active solution within the receptacle: solvent, liquid component, gel component, solid component, or any combination of those. The following components may be decomposed to produce the active solution within the receptacle: solvent, liquid component, gel component, solid component, or any combination of those.

The components may be added the following approaches: introduction from additional vessel; inserting solid element; inserting tablet, capsule or pellet; melting; destruction of gel capsule or microspheres filled with the component; destruction of impermeable barrier between components; unwrapping a roll of tape holding the component; or any combination of those. The components may be dissolved via: vibration, heating, melting, chemical or electrical shift of pH, radiation such as light, or any combination of those. The components may be involved in chemical reaction via: vibration, heating, melting, chemical or electrical shift of pH, radiation such as light, or any combination of those. The component may be decomposed via: vibration, heating, cooling, melting, chemical or electrical shift of pH, radiation such as light, or any combination of those.

The components of the active solution may be delivered in the following forms: pure form, in solution, in suspension, in emulsions, in liposomes, in synthetic or natural microspheres, microsponges or other known microencapsulation vehicles, or any combination of those.

In another variation, the receptacles set forth above are connected to additional vessel containing the following liquids: neutral solvent for producing the active solution within the receptacle; liquid component for producing the active solution within the receptacle; disinfectant; liquid for decomposition of the active solution after treatment; cosmetic ingredient; or any combination of those. In a refinement, the receptacles are disposable.

In still another variation, receptacles 18, 19 include one active solution. Examples of such solutions include, solutions for disruption of blockage of the acne channel, solutions facilitating the drainage of degraded matter from the channel, solutions for disinfecting the channel, a solution for healing the channel, solutions for masking the area of affected skin, and multi-functional solutions.

In a variation, receptacles 18, 19 contain sections for multiple active solutions. Examples of such solutions include, but are not limited to, solutions for disruption of blockage of the acne channel, solutions facilitating the drainage of degraded matter from the channel (e.g., clogged pore), solutions for disinfecting the channel, solutions for healing the channel, solutions for masking the area of affected skin, and multi-functional solutions.

Device 10 also includes a counter or dispersive electrode. In variations, the counter or dispersive electrode 16 is applied to the skin in places spaced from the electrophoretic electrode: place in close proximity to the electrophoretic electrode, such as area surrounding the acne, hand of the patient, area including an active point connected to the active points in close proximity to the acne, or any combination of those.

In another variation, device 10 includes one or more enhancing electrodes or enhancing component devices. Enhancing electrodes are designed to provide electrical influence on patient's skin, muscles and other tissues adjacent to the blocked channel and on the matter in the channel, thus enhancing and accelerating treating, drainage, disinfecting, healing and masking. Enhancing component devices are sub-systems included in device 10 that are utilized to improve or enhance the treatment of the skin condition.

Voltage to the electrodes and enhancing component devices is supplied in any number of methods known to those skilled in the art. Examples of such methods include, but are not limited to, direct electrical contact with the voltage source or with electrical circuit of the control system; capacitive induction; electromagnetic induction; or any combinations of those.

In a refinement of the present embodiment, electrodes are provided with the following means for enhancing the electrical contact of electrode 14 with skin: micro-needles penetrating the top layer of skin; moisturizing means such as electroconductive hydrating gel or sponge-like pad filled with hydrating electroconductve liquid; means for activating the eccrine sweat glands in area under and adjacent to the electrode; or any combinations of those. The following hydrating liquids may be used: water; saline solution within a range of 0.001-10%; polypropylene glycol; polyethylene glycol; polyvinyl glycol; or any mixtures of those.

The active solutions that are delivered by device 10 include a number of components that are effective it treating skin conditions such as acne. Examples of such components include, but are not limited to, alkali aqueous solutions having a pH value from 7.5 to about 11, Vitamin C, Vitamin E, Vitamin A, Vitamin K, Vitamin F, Retin A (Tretinoin), Adapalene, Retinol, Hydroquinone, Kojic acid, a growth factor, echinacea, an antibiotic, an antifungal, an antiviral, a bleaching agent, a cleansing agent, an alpha hydroxy acid, a beta hydroxy acid, salicylic acid, antioxidant triad compound, a seaweed derivative, a salt water derivative, an antioxidant, a phytoanthocyanin, epigallocatechin-3-ganate, a phytonutrient, a botanical product, a herbaceous product, a hormone, an enzyme, a mineral, a genetically engineered substance, a cofactor, a catalyst, an antiaging substance, insulin, trace elements (including ionic calcium, magnesium, etc), minerals, Rogaine, a hair growth stimulating substance, a hair growth inhibiting substance, a dye, a natural or synthetic melanin, a metalloproteinase inhibitor, proline, hydroxyproline, an anesthetic substance, chlorophyll, copper chlorophyllin, chloroplasts, carotenoids, bacteriochlorophyll, phycobilins, carotene, xanthophyll, anthocyanin, silver-containing compounds, and derivatives, sub-components, and analogs of the above, both natural and synthetic, or any mixtures of those. This active solution may be used in amount between 0.1 and 3 cc. Particularly useful as an active solution is water-based solution (e.g., a saline solution) capable of producing hydroxyl ions when a voltage is applied to electrode 14. U.S. Pat. No. 4,979,938 discloses solutions and electrode configurations which may be used in the device of the present application. The entire disclosure of this application is hereby incorporated by reference.

In another variation of the present embodiment, device 10 includes components that activate eccrine sweat glands. Such component may act by mechanical stimulation, heating, chemical irritation, electrical stimulation, optical stimulation, or any combinations of those.

As set forth above, in a variation of the present embodiment, device 10 include sensor 30. In one refinement, sensor 30 detects the characteristics distinguishing different levels of inflammation of the skin disorder such as: mechanical strength and elasticity of skin in damaged area; absorption of vibration; temperature and temperature gradient; pH value of skin and sweat; absorption of chemical and biochemical substances; presence or absence of chemical and biochemical substances in skin and sweat; electrical potential, electrical resistance and impedance of skin in the damaged area; electrical potential of active points related to the damaged area; absorption of electromagnetic radiation; color of skin; absorption of visual, infrared and ultraviolet light; presence or absence of biological reactions on the surface of skin; or any combination of those. In another refinement, sensor distinguishes the following levels of inflammation: subclinical acne, comedonal acne, mild acne, moderate acne, severe nodular acne, and severe cystic acne.

In another variation of the present embodiment, portable device 10 includes one or more of the following auxiliary component devices—a device for drainage of degraded matter from unblocked channel; device for disinfection of unblocked channel; device for healing of unblocked channel; and device for masking of treated skin disorder. Examples of drainage devices include wiping drainage device, sponging drainage device, suction drainage device, external pressure drainage device, muscle contraction drainage device, external flow drainage device, adhesion drainage device, capillary drainage device, or any combination of those. Disinfection of the drained channel may be accomplished by a solid disinfectant, a liquid disinfectant, gaseous disinfectant, cold plasma, or any combination of those. A device for healing of unblocked channel can be the following: device supplying the medication promoting the healing; device supplying stem cells; electro-stimulating healing device; or any combination of those. A device for masking of treated skin can be the following: skin decolorizing device, skin colorizing device, temporary tattooing device, powdering device, device applying crème foundation, device applying topical agents, device applying redness reduction components, device applying skin cell conditioning substances, or any combinations of those.

In still other variations, portable device 10 further includes devices for enhancing treatment of the skin condition. Examples of such devices include, but are not limited to, devices for preliminary penetration enhancement; devices for stretching and contracting skin, muscles and tissues; vibration devices; heating devices; cooling devices; moisturizing devices; drying devices; devices modifying pH; devices introducing chemicals, ions and radicals; devices applying electrical current and pulses; radiation devices, such as laser; devices influencing acupuncture active points; and combinations thereof.

Examples of devices for preliminary penetration enhancement include one or more of the following: device for enzyme peel, device for microderm abrasion, device for solvent stripping, device for tape stripping, device for scrubbing, device for laser ablation, device for laser vaporization, device for chemical peeling, device for electrical stimulation, device for laser treatments using high peak power and short pulse durations, ultrasound device, heating device, cooling device, or any combinations of those.

Examples of methodology for contacting the electrodes to the skin of a person include mechanical pressing to skin; suction; adhesion; pinching; or any combination of those. Similarly, sensor 30 can be attached by mechanical pressing to skin; suction; adhesion; pinching; or any combination of those. The additional enhancing devices may be attached by mechanical pressing to skin; suction; adhesion; pinching; or any combination of those.

In a variation of the present invention, a device for treating the receptacle is provided when the receptacle is disposable. Examples of such devices include, but are not limited to, an encapsulation device, a compacting device, a device for decomposition of active liquid, a device for decomposition of degraded matter drained from unblocked channel, a device for disinfection of surfaces of the receptacle, and combinations thereof.

Figure 4A:
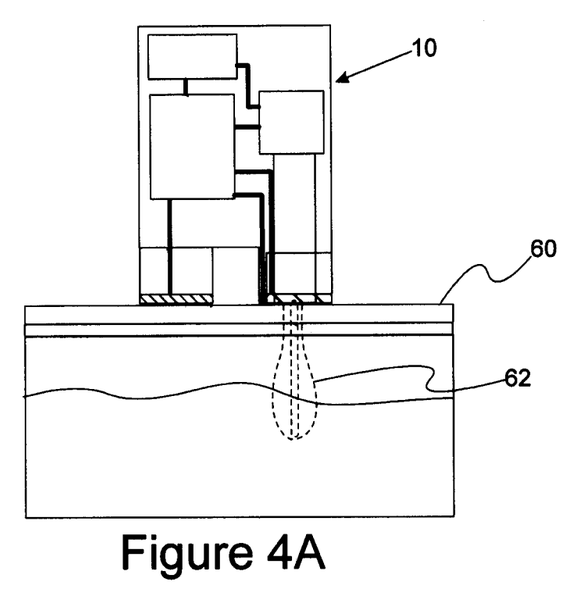
FIG. 4A is a schematic illustration showing the device of FIGS. 1A and 1B treating a skin condition.
Figure 4B:
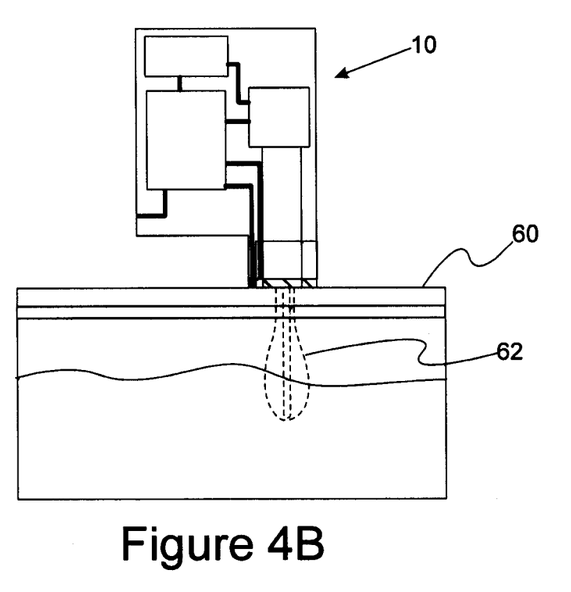
FIG. 4B is a schematic illustration showing the device of FIGS. 2A and 2B treating a skin condition.

In another embodiment of the present invention, a method for treating acne, furuncles and similar skin disorders characterized by blocked channels in the skin is provided. The method of this embodiment is advantageously performed with the devices set forth above. FIG. 4A is a schematic illustration showing the device of FIGS. 1A and 1B treating a skin condition while FIG. 4B is a schematic illustration showing the device of FIGS. 1A and 1B treating a skin condition. In these figures, device 10 contacts skin 60 to treated blocked hair follicle 62.

Figure 5:
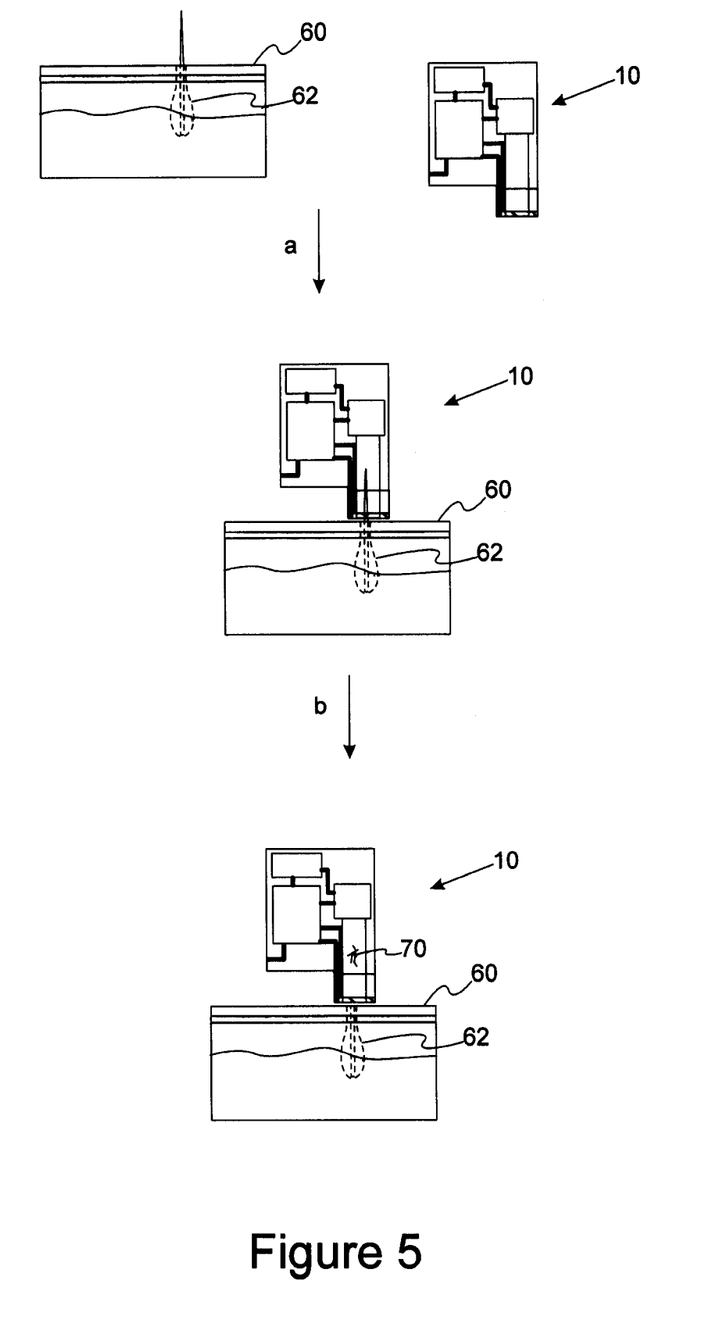
FIG. 5 is a schematic flowchart illustrating use of devices for treating a skin condition.

With reference to FIG. 5, a flowchart illustrating the method of this embodiment is provided. The method includes an operating step in which a person's skin is contacted with at least electrode 14 of device 10 is step a). In one variation the electrode of FIG. 3A is utilized. At voltage is applied to electrode 14 so that an active composition is transported to the skin. In another variation, the electrode of FIG. 3B is utilized. In this variation a voltage is applied to electrode 14 so that an active component for treating a skin condition is transported to the skin. In step b), material 70 is removed from the skin condition through channel 22 by the action of pump 24 (drainage step). In still another variation, the electrode of FIG. 3C is utilized. In this variation, electrode 14 includes two receptacles that may contain different composition. A voltage is applied to each section of electrode 14 independently so that active components from each reservoir are independently delivered to the skin. In this variation, electrode 14 optionally includes channel 22 to remove material from the skin condition through the action of pump 24.

Optionally, if sensor 30 is present, the skin is also contacted with this sensor. In another variation, other component devices if present in device 10 are also contacted with the skin. Example of such other component devices include component devices for enhancing treatment to the skin of a patient; diagnosing the level of inflammation of the skin disorder via interpreting a signal from the sensor; adjusting the characteristics of the control system and the devices for enhancing treatment according to diagnosed level of inflammation of the skin disorder; adjusting the content of the active solution according to diagnosed level of inflammation of the skin disorder; supplying the active solution to the receptacle; operating the portable device so that an electrical voltage is supplied from the voltage source through the control system to the electrodes and the devices for enhancing treatment, to thereby controllably influence the blocked channel; continuing the operation of portable device for a time sufficient to disrupt the blockage of the channel in skin affected by disorder; establishing a controllable drainage of degraded matter from the channel; disinfecting the channel; healing the channel; and masking an area of affected skin for a period of healing.

In addition to the operating step, the method of the present embodiment also includes a diagnosing step in which sensor 30 is used to assist in the diagnosis of the state of the skin condition being treated. In another variation, the method includes a drainage step in which material is removed from the skin via a drainage system that includes channel 22 and pump 24. In still another variation, the method includes one or more of the following steps: a disinfecting step, a healing step, and a masking step.

In a variation of the present embodiment, the treatment duration is from about 0.1 second to about 30 minutes. The accumulated treatment duration depends on level of inflammation of the skin disorder. In a refinement, accumulated treatment duration is from about 0.1 second to about 1 hour. The magnitude of the voltage applied to electrode 14 is typically form about 0.01V to 10V while the magnitude of current through the treated area is typically from about 0.01 mA to about 10 mA.

The portable device can also include component devices for enhancing various factors that improve the treatment at different steps: diagnosing step, operating step, drainage step, disinfecting step, healing step, and masking step.

At the diagnosing step, the following factors can improve the treatment: stretching and contracting skin, muscles and tissues; vibration; heating; cooling; moisturizing; drying; modifying pH; introducing chemicals, ions and radicals; applying electrical current and pulses; radiation, such as laser radiation; influencing acupuncture active points; or any combination of those.

At the operating step, the following factor can improve the treatment: preliminary penetration enhancement; stretching and contracting skin, muscles and tissues; vibration; heating; cooling; moisturizing; drying; modifying pH; introducing chemicals, ions and radicals; applying electrical current and pulses; radiation, such as laser radiation; influencing acupuncture active points; or any combination of those. Preliminary penetration enhancement may use the following procedures: enzyme peel, microderm abrasion, solvent stripping, tape stripping, scrubbing, laser ablation, laser vaporization, chemical peeling, electrical stimulation, laser treatments using high peak power and short pulse durations, ultrasound, heating, cooling, or any combinations of those.

At the drainage step, the following factors can improve the treatment: stretching and contracting skin, muscles and tissues; vibration; heating; cooling; moisturizing; drying; modifying pH; introducing chemicals, ions and radicals; applying electrical current and pulses; radiation, such as laser radiation; influencing acupuncture active points; or any combination of those.

At disinfecting step, the following factors can improve the treatment: stretching and contracting skin, muscles and tissues; vibration; heating; cooling; moisturizing; drying; modifying pH; introducing chemicals, ions and radicals; applying electrical current and pulses; radiation, such as laser radiation; influencing acupuncture active points; or any combination of those.

At healing step, the following factors can improve the treatment: stretching and contracting skin, muscles and tissues; vibration; heating; cooling; moisturizing; drying; modifying pH; introducing chemicals, ions and radicals; applying electrical current and pulses; radiation, such as laser radiation; influencing acupuncture active points; or any combination of those.

At masking step, the following factors can improve the treatment: stretching and contracting skin, muscles and tissues; vibration; heating; cooling; moisturizing; drying; modifying pH; introducing chemicals, ions and radicals; applying electrical current and pulses; radiation, such as laser radiation; influencing acupuncture active points; or any combination of those.

The suggested portable device may be used at all or some of the following levels of inflammation: subclinical acne, comedonal acne, mild acne, moderate acne, severe nodular acne, and severe cystic acne.

The level of inflammation may be diagnosed based on measurement of the following characteristics: mechanical strength or elasticity of skin in damaged area; absorption of vibration; temperature or temperature gradient; pH value of skin or sweat; absorption of chemical or biochemical substances; presence or absence of chemical or biochemical substances in skin or sweat; electrical potential, electrical resistance or impedance of skin in the damaged area; electrical potential of active points related to the damaged area; absorption of electromagnetic radiation; color of skin; absorption or reflection of visual, infrared or ultraviolet light; presence or absence of biological reactions on the surface of skin; or any combination of those.

The characteristics of control system may be adjusted during the following operations: determination of level of inflammation of acne; establishing the parameters for treatment; determination of content of the active solution suitable for the treatment; controlling and modifying the parameters for treatment in the process of the treatment; terminating the treatment as soon as the blockage of the channel is disrupted; controlling the process of drainage of degraded matter from the channel, process of disinfecting and process of healing of the channel; and providing control for masking an area of affected skin for a period of healing. The following characteristics may be adjusted: accumulated duration of treatment, duration of current treatment session, magnitude of applied voltage or current, character of voltage or current, duration and frequency of pulses of voltage or current, waveform of pulses of voltage or current, slew rates of transition periods, polarity of voltage or current, and dose of electrical charge delivered to the treated area.

Adjustment of enhancing devices depends on the level of inflammation and stage at which the enhancing device is operating: diagnosing step, operating step, drainage step, disinfecting step, healing step, or masking step.

Improvement of the skin treatment may be enhanced by controllable modification of following actions: preliminary penetration enhancement; stretching and contracting skin, muscles and tissues; vibration; heating; cooling; moisturizing; drying; modifying pH; introducing chemicals, ions and radicals; applying electrical current and pulses; radiation, such as laser radiation; influencing acupuncture active points; or any combinations of those. Adjustment of preliminary penetration enhancement consists of controllable modification of action: enzyme peel, microderm abrasion, solvent stripping, tape stripping, scrubbing, laser ablation, laser vaporization, chemical peeling, electrical stimulation, laser treatments using high peak power and short pulse durations, ultrasound, heating, cooling, or any combinations of those.

The content of active solution may be adjusted in the following ways: replacement of receptacles with the active solutions; switching between sections of the multi-solution receptacle; modification of the active solution inside the receptacle; injection of the active solution into the receptacle; or any combination of those.

The active solution may be modified within the receptacle prior to or during the treatment in the following ways: adding at least one component of the active solution into the receptacle; dissolving at least one component of the active solution; chemical reaction between components of the active solution; decomposition of at least one component of the active solution; or any combination of those.

The following components may be added to modify the active solution within the receptacle: solvent, liquid component, gel component, solid component, or any combination of those. The following components may be dissolved to modify the active solution within the receptacle: liquid component, gel component, solid component, or any combination of those. The following components may be reacting to modify the active solution within the receptacle: solvent, liquid component, gel component, solid component, or any combination of those. The following components may be decomposed to modify the active solution within the receptacle: solvent, liquid component, gel component, solid component, or any combination of those.

The components may be added via: introduction from additional vessel; inserting solid element; inserting tablet, capsule or pellet; melting; destruction of gel capsule or microspheres filled with the component; destruction of impermeable barrier between components; unwrapping a roll of tape holding the component; or any combination of those. The components may be dissolved via: vibration, heating, melting, chemical or electrical shift of pH, radiation such as light, or any combination of those. The components may be involved in chemical reaction via: vibration, heating, melting, chemical or electrical shift of pH, radiation such as light, or any combination of those. The components may be decomposed via: vibration, heating, cooling, melting, chemical or electrical shift of pH, radiation such as light, or any combination of those.

The components of the active solution may be delivered in the following forms: pure form, in solution, in suspension, in emulsions, in liposomes, in synthetic or natural microspheres, microsponges or other known microencapsulation vehicles, or any combination of those.

The active solution may be supplied to the receptacle in the following ways: preliminary filling the receptacle with ready-to-use active solution; preliminary filling the receptacle with components of the active solution followed by preparation of ready-to-use active solution prior to or during its use; providing a flow of the active solution through the receptacle; periodical adding the active solution to the receptacle and withdrawal of exhausted active solution; or any combinations of those.

The active solution may be prepared within the receptacle via: adding at least one component of the active solution into the receptacle; dissolving at least one component of the active solution; chemical reaction between components of the active solution; decomposition of at least one component of the active solution; or any combination of those.

The following components may be added to prepare the active solution within the receptacle: solvent, liquid component, gel component, solid component, or any combination of those. The following components may be dissolved to prepare the active solution within the receptacle: liquid component, gel component, solid component, or any combination of those. The following components may be reacting to prepare the active solution within the receptacle: solvent, liquid component, gel component, solid component, or any combination of those. The following components may be decomposed to prepare the active solution within the receptacle: solvent, liquid component, gel component, solid component, or any combination of those.

The components may be added via: introduction from additional vessel; inserting solid element; inserting tablet, capsule or pellet; melting; destruction of gel capsule or microspheres filled with the component; destruction of impermeable barrier between components; unwrapping a roll of tape holding the component; or any combination of those. The components may be dissolved via: vibration, heating, melting, chemical or electrical shift of pH, radiation such as light, or any combination of those. The components may be involved in chemical reaction via: vibration, heating, melting, chemical or electrical shift of pH, radiation such as light, or any combination of those. The components may be decomposed via: vibration, heating, cooling, melting, chemical or electrical shift of pH, radiation such as light, or any combination of those. The components of the active solution may be delivered for preparation in the following forms: pure form, in solution, in suspension, in emulsions, in liposomes, in synthetic or natural microspheres, microsponges or other known microencapsulation vehicles, or any combination of those.

The voltage to electrodes and enhancing devices may be supplied via: direct electrical contact with the voltage source or with electrical circuit of the control system; capacitive induction; electromagnetic induction; or any combinations of those. The following controllable factors on a blocked channel are suggested: supplying negative ions and radicals into the channel and surrounding area; supplying positive ions and radicals into the channel and surrounding area; applying treatment enhancing composition to the channel and surrounding area; or any combinations of those. The following factors may be used to enhance treatment: preliminary penetration enhancement; stretching and contracting skin, muscles and tissues; vibration; heating; cooling; moisturizing; drying; modifying pH; introducing chemicals, ions and radicals; applying electrical current and pulses; radiation, such as laser radiation; influencing acupuncture active points; or any combination of those. Penetration may be preliminary enhanced via the following procedures: enzyme peel, microderm abrasion, solvent stripping, tape stripping, scrubbing, laser ablation, laser vaporization, chemical peeling, electrical stimulation, laser treatments using high peak power and short pulse durations, ultrasound, heating, cooling, or any combinations of those.

The controllable influence of device 10 on blocked channels (e.g., pore hair follicles) may be further improved via use of feedback from sensor for more precise adjustment of factors based on changes in state of the blocked channel; this feedback is based on measurement of the following characteristics: mechanical strength and elasticity of skin in damaged area; absorption of vibration; temperature and temperature gradient; pH value of skin and sweat; absorption of chemical and biochemical substances; presence or absence of chemical and biochemical substances in skin and sweat; electrical potential, electrical resistance and impedance of skin in the damaged area; electrical potential of active points related to the damaged area; absorption of electromagnetic radiation; color of skin; absorption or reflection of visual, infrared and ultraviolet light; presence or absence of biological reactions on the surface of skin; or any combination of those. The sufficient time for disrupting blockage is determined via visual or instrumental detection of disruption.

The instrumental detection of disruption of the blockage is based on measurement of the following characteristics: mechanical strength and elasticity of skin in damaged area; absorption of vibration; temperature and temperature gradient; pH value of skin and sweat; absorption of chemical and biochemical substances; presence or absence of chemical and biochemical substances in skin and sweat; electrical potential, electrical resistance and impedance of skin in the damaged area; electrical potential of active points related to the damaged area; absorption of electromagnetic radiation; color of skin; absorption or reflection of visual, infrared and ultraviolet light; presence or absence of biological reactions on the surface of skin; or any combination of those.

The following variants of drainage may be used: wiping drainage, sponging drainage, suction drainage, external pressure drainage, muscle contraction drainage, external flow drainage, adhesion drainage, capillary drainage, or any combination of those.

The drained channel may be disinfected with solid disinfectant, liquid disinfectant, gaseous disinfectant, cold plasma, or any combination of those. The following disinfectants may be used: alcohols, iodophor, hydrogen peroxide, anolyte of electrically activated water, or any combination of those.

The following variants of healing of unblocked channel may be facilitated by suggested portable device: natural healing, medication-promoted healing, stem-cell promoted healing, electro-stimulated healing, or any combination of those.

The treated skin disorder may be masked via: skin decolorizing, skin colorizing, temporary tattooing, powdering, applying crème foundation, applying topical agents, applying redness reduction components, applying skin cell conditioning substances, or any combinations of those.

The topical agents are the compositions and derivatives and analogs of the following substances: hair dyes; vegetable dyes; food coloring; fabric dyes; tissue stains; shoe or leather dyes; other plant products, such as flavonols, chlorophyll, copper chlorophyllin, bacteria chlorophylls; carotenoids; enzymes; monoclonal antibodies; any immunological agent; genetically engineered agent; benign infectious agents, whether naturally occurring or genetically engineered, including various bacteria that normally reside on the skin such as acne bacteria; antibiotics; agents which attach to sebocytes in the sebaceous gland or duct cells directly, whether by topical or systemic agents that localize in these target tissues, including antibodies or antibody-chromophore compounds of these structures; topical compositions that include a quantity of a naturally occurring chromophore such as chlorophyll, chlorophyllin, polyporphyin, bacteriochlorophyll, protopolyporphyin; or any combinations of those.

The following components may be used as skin cell conditioning components: chromium component, vitamin C source, burdock root, yellow dock root, horsetail extract, a catechin-based composition, a vitamin $B_1$ source, a vitamin $B_2$ source, a vitamin $B_3$ source, a vitamin $B_5$ source, a vitamin E source, amino acid component, a magnesium component, a selenium component, biotin, or any combinations of those.

The following redness reduction components may be used: a zinc compound in an amount greater than 15 mg to about 96 mg, and a Vitamin A source in an amount sufficient to reduce the redness and blemishes associated with the skin disorder.

The following treatment of disposable receptacle may be useful: encapsulation; compacting; decomposition of active liquid; decomposition of degraded matter drained from unblocked channel; disinfection of surfaces of the receptacle; or any combinations of those.

A treatment of acne, furuncles or other similar skin disorders which are characterized by blocked channels in the skin includes attaching the electrodes, sensor and devices for enhancing treatment to the skin of a patient, diagnosing the level of inflammation of the skin disorder via interpreting a signal from the sensor, adjusting the characteristics of the control system and the devices for enhancing treatment according to diagnosed level of inflammation of the skin disorder, adjusting the content of the active solution according to diagnosed level of inflammation of the skin disorder, applying electrical voltage through the control system to the electrodes and devices for enhancing treatment to thereby produce ions in the active solution which are caused to move into the hair follicles of the skin affected by the disorder, produce other influences on the disorder and surrounding tissues, and thereby controllably influence the blocked channel for a time sufficient to modify pH value in the blocked channel to a value of more than 7 units and disrupt the blockage of the follicles, providing controllable drainage of the degraded matter from the channel, disinfecting the channel, healing the channel, and masking an area of affected skin for a period of healing.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed:

1. A device for treating a skin disorder comprising:
   a first delivery system for administering a first composition to the skin disorder, the first delivery system comprising:
   a first electrode for delivering the first composition;
   a first counter electrode;
   a drainage system for removing material from a person's skin;
   a second delivery system for administering a second composition to the skin disorder, the second delivery system comprising:
   a second electrode for delivering the second composition;
   a second counter electrode; and
   a control system for powering and controlling the first and second delivery systems.

2. The device of claim 1 wherein the first electrode comprises a first receptacle and a first semipermeable base and the second electrode comprises a second receptacle and a second semipermeable base.

3. The device of claim 1 wherein the first electrode and the second electrode each independently comprise an active solution for treating a skin condition.

4. The device of claim 3 wherein the active solution is selected from the group consisting of an alkali aqueous solutions having a pH value from 7.5 to about 11, Vitamin C, Vitamin E, Vitamin A, Vitamin K, Vitamin F, Retin A (Tretinoin), Adapalene, Retinol, Hydroquinone, Kojic acid, a growth factor, echinacea, an antibiotic, an antifungal, an antiviral, a bleaching agent, a cleansing agent, an alpha hydroxy acid, a beta hydroxy acid, salicylic acid, antioxidant triad compound, a seaweed derivative, a salt water derivative, an antioxidant, a phytoanthocyanin, epigallocatechin-3-ganate, a phytonutrient, a botanical product, a herbaceous product, a hormone, an enzyme, a mineral, a genetically engineered substance, a cofactor, a catalyst, an antiaging substance, insulin, trace elements (including ionic calcium, magnesium, etc), minerals, a hair growth stimulating substance, a hair growth inhibiting substance, a dye, a natural or synthetic melanin, a metalloproteinase inhibitor, proline, hydroxyproline, an anesthetic substance, chlorophyll, copper chlorophyllin, chloroplasts, carotenoids, bacteriochlorophyll, phycobilins, carotene, xanthophyll, anthocyanin, silver-containing compounds, and combinations thereof.

5. The device of claim 4 wherein the active solution comprises a water-based solution capable of producing hydroxyl ions when a voltage is applied to the first electrode.

6. The device of claim 4 wherein the control system includes a voltage source.

7. The device of claim 1 wherein the drainage system includes:
   a channel for removing material from the person's skin; and
   a pump in communication with the channel.

8. A device for treating a skin disorder comprising:
   a first delivery system for administering a first composition to the skin disorder, the first delivery system comprising:
   a first electrode for delivering the first composition;
   a first counter electrode;
   a second delivery system for administering a second composition to the skin disorder, the second delivery system comprising:
   a second electrode for delivering the second composition;
   a second counter electrode; a drainage system including:
   a channel for removing material from a person's skin; and
   a pump in communication with the channel; and a control system for powering and controlling the first electrode, the first counter electrode, the second electrode, the second counter electrode.

9. The device of claim 8 wherein the first electrode comprises a first receptacle and a first semipermeable base and the second electrode comprises a second receptacle and a second semipermeable base.

10. The device of claim 8 wherein the first electrode and second electrode each independently comprise an active solution for treating a skin condition.

* * * * *